United States Patent
Yang et al.

(10) Patent No.: US 11,021,756 B2
(45) Date of Patent: Jun. 1, 2021

(54) MIRNA MARKERS FOR THE DIAGNOSIS OF OSTEOSARCOMA

(71) Applicant: Zuozhang Yang, Yunnan (CN)

(72) Inventors: Zuozhang Yang, Yunnan (CN); Ya Zhang, Yunnan (CN); Yihao Yang, Yunnan (CN); Xiaojuan Li, Yunnan (CN); Dongqi Li, Yunnan (CN); Junfeng Xia, Yunnan (CN); Su Li, Yunnan (CN); Zhaoxin Zhang, Yunnan (CN); Huiling Li, Yunnan (CN); Yanjin Chen, Yunnan (CN)

( * ) Notice: Subject to any disclaimer, the term of this patent is extended or adjusted under 35 U.S.C. 154(b) by 0 days.

(21) Appl. No.: 16/067,889

(22) PCT Filed: Nov. 21, 2016

(86) PCT No.: PCT/CN2016/106567
§ 371 (c)(1),
(2) Date: Jul. 3, 2018

(87) PCT Pub. No.: WO2017/118230
PCT Pub. Date: Jul. 13, 2017

(65) Prior Publication Data
US 2020/0224275 A1    Jul. 16, 2020

(30) Foreign Application Priority Data

Jan. 4, 2016   (CN) .......................... 201610003247.8
Jan. 4, 2016   (CN) .......................... 201610003305.7
Jul. 21, 2016  (CN) .......................... 201610578751.0

(51) Int. Cl.
*A61K 48/00*   (2006.01)
*C12N 15/11*   (2006.01)
(Continued)

(52) U.S. Cl.
CPC ..... *C12Q 1/6886* (2013.01); *C12Q 2600/158* (2013.01); *C12Q 2600/178* (2013.01)

(58) Field of Classification Search
CPC ............ C12Q 1/6886; C12Q 2600/118; C12Q 2600/178; C12N 2310/141; C12N 15/113;
(Continued)

(56) References Cited

U.S. PATENT DOCUMENTS

2013/0012405 A1   1/2013   Duttagupta et al.
2013/0142728 A1*  6/2013   Beaudenon-Huibregtse ............... C12Q 1/6886
                                                                           424/1.11
(Continued)

FOREIGN PATENT DOCUMENTS

CN    102421916    4/2012
CN    103476947    12/2013
(Continued)

OTHER PUBLICATIONS

International Search Report for PCT/CN2016/106567, dated Feb. 14, 2017, 6 pages.
(Continued)

*Primary Examiner* — Terra C Gibbs
(74) *Attorney, Agent, or Firm* — Nixon & Vanderhye, PC

(57) ABSTRACT

The present invention discloses the use of miR-4714, miR-4521, and miR-1292 as diagnostic markers for osteosarcoma. High-throughput sequencing and QPCR experiments prove that the levels of miR-4714, miR-4521, and miR-1292 in the blood of normal and osteosarcoma patients are significantly different, and therefore miR-4714, miR-4521, and miR-1292 can be used as a molecular marker for the diagnosis of osteosarcoma for developing products for the diagnosis of osteosarcoma. The diagnostic product has the
(Continued)

following advantages: non-invasive, rapid, sensitive, and has broad application prospects in clinical practice.

5 Claims, 2 Drawing Sheets

Specification includes a Sequence Listing.

(51) Int. Cl.
*C07H 21/02* (2006.01)
*C07H 21/04* (2006.01)
*C12Q 1/6886* (2018.01)

(58) Field of Classification Search
CPC ... C12N 15/1138; A61K 48/00; A61K 31/713
See application file for complete search history.

(56) References Cited

U.S. PATENT DOCUMENTS

| | | | |
|---|---|---|---|
| 2014/0206852 | A1 | 7/2014 | Hoge et al. |
| 2015/0057165 | A1* | 2/2015 | Dave ................ C12Q 1/6886 506/7 |

FOREIGN PATENT DOCUMENTS

| | | |
|---|---|---|
| CN | 104372007 | 2/2015 |
| CN | 105441565 | 3/2016 |
| CN | 105561341 | 5/2016 |
| WO | 2014/044827 | 3/2014 |
| WO | WO 2014/113089 A2 | 7/2014 |
| WO | WO-2014113089 A2 * 7/2014 ......... A61K 48/0058 |
| WO | WO-2014179765 A2 * 11/2014 .......... C12Q 1/6886 |

OTHER PUBLICATIONS

Wang, X.F. et al. "Serum MicroRNA-4521 is a Potential Biomarker for Focal 1-10 Cortical Dysplasia with Refractory Epilepsy.", Neiirochem. Res., vol. 41, Dec. 8, 2015, pp. 905-912.

Sampson, V.B. et al. "MicroRNAs and Potential Targets in Osteosarcoma: Review.", Frontiers in Pediatrics., vol. 3, Aug. 24, 2015, article 69, pp. 1-13.

Camps, C. et al. "Integrated Analysis of MicroRNA and mRNA Expression and Association with HIF Binding Reveals the Complexity of MicroRN A Expression Regulation under Hypoxia.", Molecular Cancer., vol. 13, No. 28, Dec. 31, 2014, pp. 1-21.

Miao, Jinglei et al. "MicroRNAs in Osteosarcoma: Diagnostic and Therapeutic Aspects.", Tumor Biol., vol. 34, Jun. 25, 2013, pp. 2093-2098.

Wang et al., "Serum MicroRNA-4521 Is a Potential Biomarker for Focal Cortical Dysplasia with Refractory Epilepsy", Neurochem Res., Dec. 8, 2015, pp. 1-8.

Sampson et al., "MicroRNAs and Potential Targets in Osteosarcoma: Review", Frontiers in Pediatrics | www.frontiersin.org; Aug. 2015 | vol. 3 | Article 69; pp. 1-13.

Camps et al., "Integrated Analysis of microRNA and mRNA Expression and Association with HIF Binding Reveals the Complexity of MicroRNA Expression Regulation Under Hypoxia", Molecular Cancer 2014, vol. 13, No. 28 Dec. 31, 2014; pp. 1-21; http://www.molecular-cancer.com/content/13/1/28.

Miao et al., "MicroRNAs in Osteosarcoma: Diagnostic and Therapeutic", Tumor Biology (2013) 34:2093-2098.

* cited by examiner

SEQUENCE LISTING

```
<160> NUMBER OF SEQ ID NOS: 9

<210> SEQ ID NO 1
<211> LENGTH: 22
<212> TYPE: RNA
<213> ORGANISM: Homo sapiens

<400> SEQUENCE: 1
gcuaaggaag uccugugcuc ag                                              22

<210> SEQ ID NO 2
<211> LENGTH: 22
<212> TYPE: RNA
<213> ORGANISM: Homo sapiens

<400> SEQUENCE: 2
ccaaccuagg uggucagagu ug                                              22

<210> SEQ ID NO 3
<211> LENGTH: 25
<212> TYPE: RNA
<213> ORGANISM: Homo sapiens

<400> SEQUENCE: 3
ugggaacggg uuccggcaga cgcug                                           25

<210> SEQ ID NO 4
<211> LENGTH: 22
<212> TYPE: DNA
<213> ORGANISM: Artificial Sequence
<220> FEATURE:
<223> OTHER INFORMATION: Forward primer

<400> SEQUENCE: 4
gctaaggaag tcctgtgctc ag                                              22

<210> SEQ ID NO 5
<211> LENGTH: 16
<212> TYPE: DNA
<213> ORGANISM: Artificial Sequence
<220> FEATURE:
<223> OTHER INFORMATION: Reverse primer

<400> SEQUENCE: 5
gtgcagggtc cgaggt                                                     16
```

```
<210> SEQ ID NO 6
<211> LENGTH: 22
<212> TYPE: DNA
<213> ORGANISM: Artificial Sequence
<220> FEATURE:
<223> OTHER INFORMATION: Forward primer

<400> SEQUENCE: 6
ccaacctagg tggtcagagt tg                                            22

<210> SEQ ID NO 7
<211> LENGTH: 25
<212> TYPE: DNA
<213> ORGANISM: Artificial Sequence
<220> FEATURE:
<223> OTHER INFORMATION: Forward primer

<400> SEQUENCE: 7
tgggaacggg ttccggcaga cgctg                                         25

<210> SEQ ID NO 8
<211> LENGTH: 17
<212> TYPE: DNA
<213> ORGANISM: Artificial Sequence
<220> FEATURE:
<223> OTHER INFORMATION: Forward primer

<400> SEQUENCE: 8
ctcgcttcgg cagcaca                                                  17

<210> SEQ ID NO 9
<211> LENGTH: 20
<212> TYPE: DNA
<213> ORGANISM: Artificial Sequence
<220> FEATURE:
<223> OTHER INFORMATION: Reverse Primer

<400> SEQUENCE: 9
aacgcttcac gaatttgcgt                                               20
```

MIRNA MARKERS FOR THE DIAGNOSIS OF OSTEOSARCOMA

CROSS REFERENCE TO RELATED APPLICATIONS

This application is the U.S. national phase of International Application No. PCT/CN2016/106567 filed 21 Nov. 2016, which designated the U.S. and claims priority to CN Patent Application No. 201610003247.8 filed 4 Jan. 2016, CN Patent Application No. 201610003305.7 filed 4 Jan. 2016, and CN Patent Application No. 201610578751.0 filed 21 Jul. 2016, the entire contents of each of which are hereby incorporated by reference.

REFERENCE TO SEQUENCE LISTING SUBMITTED ELECTRONICALLY

The content of the electronically submitted sequence listing (Name: 6701_0004_Sequence_Listing_ST25.txt; Size: 1.92 kilobytes; and Date of Creation: Mar. 13, 2020) filed on Mar. 13, 2020 is incorporated herein by reference in its entirety.

TECHNICAL FIELD

The invention belongs to the field of biomedicine and relates to miRNA diagnostic markers of osteosarcoma. The specific miRNA diagnostic markers are miR-4521, miR-4714-3p and miR-1292.

BACKGROUND OF RELATED ART

Osteosarcoma is a malignant tumor that originates from the skeleton. Its incidence is the highest among primary bone malignant tumors. Osteosarcomas are divided into a variety of pressure types, and the chondroblastoma osteosarcoma as a subtype of common osteosarcoma has no significant difference in clinical treatment and prognosis with other common osteosarcoma. 75% of osteosarcoma patients are adolescents with more males (male:female equal to 1.5:1). The degree of malignancy is very high and they are prone to early lung metastasis. The prognosis is extremely poor. Previously discovered osteosarcoma was mostly treated with amputation. Even so, the survival rate of patients within 5 years after operation is only 5-20%. This brings great mental harm to patients and their families, and it also brings heavy economic burden to society and even the country.

So far, the cause of osteosarcoma is still unclear. In most cases, there are widespread sporadic features, that is, there is no known genetic or environmental factor. Major domestic and foreign laboratories are exploring the possible involvement of cancer stem cells in the formation of bone tumors. In the normal state of cells, part of the genes are involved in DNA repair and tumor suppression pathways, which helps maintain the integrity of the cellular processes. Defects in these genes may be involved in the pathogenesis of osteosarcoma. In addition, the role of chromosomal changes in the pathogenesis of osteosarcoma has also attracted increasing attention, such as the acquisition of function of chromosome 1, loss of function on chromosome 9, and loss of heterozygosity of some chromosomes.

Radical surgery is still the first choice for the treatment of osteosarcoma. At the same time, high dose chemotherapy is given before surgery. Current effective chemotherapy drugs include cisplatin, doxorubicin, and Methotrexate. With the expansion of radical surgery and high-dose chemotherapy, the five-year survival rate of osteosarcoma patients has increased to about 70%. However, there are still a considerable number of patients who have undergone comprehensive treatment have tumor recurrence and distant metastasis. The recurrence and distant metastasis of tumors have greatly reduced the survival rate of osteosarcoma patients. Although many studies have focused on improving the prognosis of osteosarcoma patients through the development of new osteosarcoma treatment methods, early detection of tumors is still critical to their prognosis. Understanding the molecular mechanisms involved in the pathogenesis of osteosarcoma will help develop new molecular biomarkers and gene-targeted therapeutic drugs.

miRNA is a small non-coding RNA molecule (ncRNAs) composed of 19 to 22 mature nucleotides. It was first discovered in 1993 by the Ambros team in the study of nematodes. To date, miRNAs are present in all plants and animals, accounting for approximately 4% of the genome. They play an important role in the occurrence, differentiation, proliferation and apoptosis of cells. In addition, based on the function of target genes, miRNAs have a wide range of regulatory effects on cancers. They can be used as tumor suppressors or tumorigenic factors. The main mechanisms of miRNA include deletions, amplifications, mutations in miRNA loci, changes in epigenetic levels, and abnormal expression of regulatory factors.

Detecting the expression level of miRNA can provide a reference for the clinical diagnosis of cancer. At present, there are few researches on the differential expression of miRNA in osteosarcoma. Finding and identifying the miRNAs related to the occurrence of osteosarcoma provide the basis for the clinical diagnosis and treatment of miRNAs, which will help early diagnosis and prognostic evaluation of osteosarcoma to a new level.

SUMMARY OF THE INVENTION

To remedy the deficiencies of the prior art, one of the objects of the present invention is to provide microRNAs that can be used to treat osteosarcoma, and the microRNAs are selected from one or more of the following groups: miR-4521, miR-4714, and miR-1292.

The second object of the present invention is to provide a diagnostic product for early diagnosis of osteosarcoma.

The third object of the present invention is to provide the use of the above microRNA.

In order to achieve the above objectives, the present invention adopts the following technical solutions:

The invention provides an application of the reagent for detecting micro RNA in preparing a diagnostic tool for osteosarcoma. The microRNA is selected from one or more of the following groups: miR-4521, miR-4714, and miR-1292.

The microRNA of the present invention includes an original miRNA, a precursor miRNA, or a mature miRNA; the initial miRNA can be cleaved and expressed as a mature miRNA in human cells; the precursor miRNA can be cleaved and expressed as a mature miRNA in human cells.

It will be appreciated that microRNAs of the invention include functional equivalents of a constitutive nucleic acid molecule, i.e., variants. "Variant" refers to one or more biologically active miRNAs that have less than 100% identity to the corresponding wild-type miRNA gene product and have a corresponding wild-type miRNA gene product. Examples of such biological activities include, but are not limited to, inhibition of cellular processes (e.g., cell differentiation, cell growth, and cell death) that occur in the development of osteosarcoma. These variants include species variants and variants resulting from one or more mutations (e.g., substitutions, deletions, and insertions) of miRNA genes. In some embodiments, the variant has at least about 70%, 75%, 80%, 85%, 90%, 95%, 98%, or 99% identity with the corresponding wild-type miRNA gene product.

It is well known to those skilled in the art that in order to ensure the stability of miRNAs, protective bases such as TT may be added to one or both ends of the miRNA, and miRNA bases may also be modified, but the function of the miRNA is not affected. Therefore, it is well known to those skilled in the art that the sequence obtained by base modification of the aforementioned microRNA or base addition at both ends without affecting the function of the microRNA described above is also included in the protection scope of the present invention.

In some specific embodiments of the present invention, the miRNA-4521 is a mature miRNA-4521, the nucleotide sequence is shown in SEQ ID NO. 1 in the sequence listing, and the miR-4714 is miR-4714-3p. The nucleotide sequence is shown in SEQ ID NO. 2 in the sequence listing, the miR-1292 is miR-1292-5p, and the nucleotide sequence is shown in SEQ ID NO. 3 in the sequence listing.

Although mature miRNAs are used in some embodiments, one skilled in the art can expect that the original miRNA and precursor miRNA will have the same technical effect as the mature miRNA because the cells have the ability to further process the primary miRNA, the precursor miRNAs into mature miRNAs.

The microRNA nucleic acid molecule of the present invention may exist in a single-stranded or double-stranded form. Mature miRNAs are predominantly in single-stranded form, whereas precursor miRNAs are partially self-complementary to form double-stranded structures. The nucleic acid molecule of the present invention may be in the form of RNA, DNA, PNA, and LNA.

Further, the reagent for detecting microRNA includes a reagent for detecting the expression level of microRNA in a sample.

Further, the tool diagnoses osteosarcoma by measuring the expression level of microRNA in the sample.

Further, the samples include blood, urine, cerebrospinal fluid, tissue fluid, sweat, saliva, and tears. Preferably, the sample is blood.

Further, the tool can diagnose osteosarcoma by detecting the expression level of microRNAs by using qRT-PCR, blot hybridization, in situ hybridization, array hybridization, gene chip or next-generation sequencing.

Among them, miRNA-4521 is down-regulated in osteosarcoma tissue. Compared with the control, when the miRNA-4521 in the subject's blood is significantly reduced, the patient could be judged to have osteosarcoma or have the risk of osteosarcoma or the patient's prognosis is not good. miR-1292 and miR-4714 are up-regulated in osteosarcoma tissues. Compared with controls, when the miR-1292 and miR-4714 in the blood of the subjects increased significantly, the patient is judged to have osteosarcoma or have the risk of osteosarcoma, or the patient's prognosis is not good.

Further, the diagnostic tools include, but are not limited to, chips, kits, test strips, and high-throughput sequencing platforms. The diagnostic tool includes an agent for detecting the expression level of the above microRNA in a sample.

Further, the kit includes primers and/or probes for the above microRNAs; the chip includes a solid phase carrier; and an oligonucleotide probe immobilized on the solid phase carrier, the oligonucleotide probe includes partial or complete sequences that specifically correspond to the above microRNAs; the test paper includes primers and/or probes for the above microRNAs; the high-throughput sequencing platform includes primers and/or probe for the above microRNAs.

The present invention provides a diagnostic tool for osteosarcoma, the diagnostic tool comprises an agent for detecting the expression level of the aforementioned microRNA in a sample.

Further, the samples include blood, urine, cerebrospinal fluid, tissue fluid, sweat, saliva, and tears. In a particular embodiment of the invention, the sample is blood.

Further, the diagnostic tool includes a kit, a chip, a test strip, and a high-throughput sequencing platform.

Further, the kit includes primers and/or probes for the aforementioned microRNAs; the chip includes a solid carrier; and oligonucleotide probes immobilized on the solid carrier, the oligonucleotide probes include partial or full sequences that specifically correspond to the aforementioned microRNAs; the test strips include primers and/or probes for the aforementioned microRNAs; the high-throughput sequencing platform includes primers and/or probes for the aforementioned microRNAs.

Further, the primers and/or probes for the aforementioned microRNA in the kit may further include primers and/or probes that have been reported in the prior art and may be used to detect the expression level of the microRNA described above. The case of multiple microRNA detection primers and/or probes placed in the same kit for the diagnosis of osteosarcoma by detecting multiple microRNA markers is also within the scope of the present invention.

Further, the on-chip immobilized oligonucleotide probe may further include an oligonucleotide probe that has been reported in the prior art and can be used to detect the expression level of the aforementioned microRNA. Placing multiple miRNA detection probes on the same chip is also included within the scope of the present invention by detecting multiple miRNA markers in combination to diagnose osteosarcoma.

According to the aforementioned sequence of microRNAs of the present invention, suitable probes for RNA blot hybridization of a given miRNA can be generated, including but not limited to having at least about 70%, 75%, 80%, 85%, 90%, 95%, 98%, 99%, or complete complementarity with the target miRNA.

Probes can be labeled with high specific radioactivity by nick translation or random primer methods. For example, a 32P-labeled nucleic acid probe with a specific radioactivity exceeding 108 cpm/microgram can be prepared by replacing existing nucleotides with highly radioactive nucleotides according to the nick translation method. Hybrid autoradiography detection can then be performed by exposing the hybridized filter to photographic film.

The preparation of the miRNA chip may adopt conventional manufacturing methods of biochips known in the art. For example, if the solid-phase carrier is a modified glass slide or a silicon wafer, the 5'-end of the probe contains an amino-modified poly-dT string. The oligonucleotide probe can be formulated into a solution, then spotted on a modified glass slide or wafer using a spotting machine, arranged in a predetermined sequence or array, and then fixed by placing it overnight to obtain the miRNA chip of the present invention. If the nucleic acid contains no amino modification, its preparation method may also refer to: "Genetic diagnostic technology-non-radioactive manual" edited by Wang Shenwu; JLerisi, VRIyer, POBROWN. Exploring the metabolic and genetic control of gene expression on a genomic scale. Science, 1997; 278: 680 and Ma Liren, Jiang Zhonghua. Biochips. Beijing: Chemical Industry Press, 2000, 1-130.

Further, the solid-phase carrier includes the solid-phase carrier and can use various common materials in the field of gene chips, such as but not limited to a nylon membrane, slides or wafers modified with reactive groups (such as aldehyde groups, amino groups, etc.), unmodified slides and plastic sheets, etc.

The microRNA of the present invention may be either natural or synthetic, or may be obtained by transfecting cells with a vector that can express DNA fragments of microRNA.

The vectors include viral vectors and eukaryotic vectors.

The viral vector can be any suitable vector including, but not limited to, retroviral vectors, adenoviral vectors, adeno-associated virus vectors, herpes viruses (eg, herpes simplex virus, vaccinia virus, and EB virus (epstein-barr virus)) vectors, and alphavirus vectors.

The eukaryotic expression vector can be any suitable expression vector, including but not limited to pCMV-Myc expression vector, pcDNA3.0 expression vector, pcDNA3.1 expression vector, pEGFP expression vector, pEF Bos expression vector, pTet expression vector, pTRE expression vector or, modified vectors based on well-known expression vectors, such as pBin438, pCAMBIA1301, and the like.

The DNA fragment that expresses the microRNA can be obtained by searching for the position and specific sequence information of the microRNA on the genome from the miRNA database (http://microrna.sanger.ac.uk/sequences/) and determining the sequence of the genome based on the genome sequence. For the position of the initial miRNA, specific primers are designed in the upstream and downstream 500-800 bp region of the initial miRNA position, and the DNA fragment expressing the microRNA is obtained by amplifying the sequence in the middle of the primer.

The "microRNA" used in the present invention is common to "miRNA" and "miR".

The "diagnosed osteosarcoma" used in the present invention includes the prediction of osteosarcoma, that is, determining whether the subject is at risk of having osteosarcoma, and also includes the diagnosis of osteosarcoma, that is, judging whether the subject has suffered from osteosarcoma or not. Tumors also include a judgment of the prognosis of osteosarcoma, that is, determining whether the subject has the possibility of recurrence or judging that the subject has relapsed.

The advantages and benefits of the present invention:

The present invention firstly finds that miR-4521, miR-4714, and miR-1292 are related to osteosarcoma. By detecting the expression of miR-4521, miR-4714, and miR-1292, it can be determined whether the subject has osteosarcoma or not, or determine whether the subject is at risk of having osteosarcoma, thereby instructing the clinician to provide the subject with a prophylactic or therapeutic regimen.

The present invention finds a new microRNA marker, which is more timely, more specific, and more sensitive than conventional detection methods, and can realize early diagnosis of osteosarcoma, thereby reducing the mortality of osteosarcoma.

DETAILED DESCRIPTION OF THE EMBODIMENT

Figure 1:
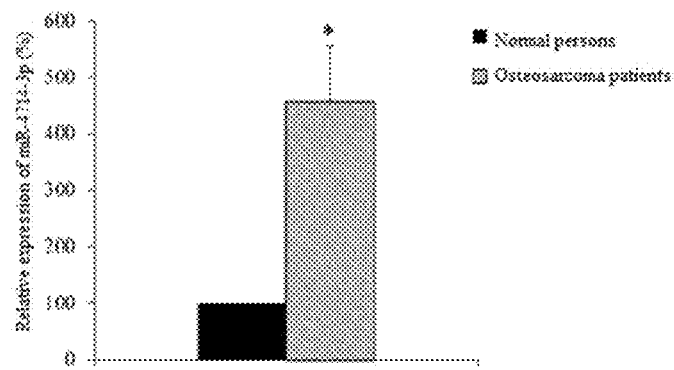
FIG. 1 shows the use of high-throughput sequencing to detect the expression of miR-4714-3p in the blood of osteosarcoma patients.

The present invention will be specifically described below by way of embodiments. It is necessary to point out here that the following embodiments are only used for further description of the present invention, and cannot be construed as limiting the scope of protection of the present invention. Those skilled in the art can make some non-essential improvements and adjustments to the present invention based on the contents of the above-mentioned invention. In the following examples, unless specifically indicated, the reagents used are analytical grade and the reagents used are commercially available. The experimental methods without specific conditions are not specified in the text, and are usually based on conventional conditions such as those described in the "Molecular Cloning Laboratory Guidebook" published by Science Press, J. Sambrook, et al. (2002), or as the conditions recommended by the manufacturer. Unless defined otherwise, all professional and scientific terms used herein have the same meaning as is familiar to those skilled in the art. In addition, any methods and materials similar or equivalent to those described may be applied to the present invention.

Example 1 High-Throughput Sequencing Screening Mirnas Associated with Osteosarcoma 1. Sample acquisition: 5 osteosarcoma patients and 5 normal persons were collected. The subjects were requested for an empty stomach for at least 12 hours, at room temperature from 7:00 am to 8:00 am in the following morning, 10 ml of venous blood was drawn into an anti-coagulation tube of ethylenediaminetetraacetic acid (EDTA) to extract PBMCs from peripheral blood mononuclear cells. 1 ml of Trizol reagent (Invitrogen) was mixed thoroughly, and specimens were stored at −80° C. for RNA extraction. All blood samples and pathological findings should be true and reliable. The study was approved by the Ethics Committee and informed consent was obtained.

2. RNA Extraction of blood mononuclear cells

Total RNA was extracted by using Invitrogen's RNA extraction kit. The steps were as follows:

(1) 1 ml of Trizol was firstly added into $1 \times 10^7$ cells. If the cryopreserved cells were directly added to Trizol, thawing was not required. After lysing and cracking, the cells were allowed to stand for 5-10 minutes at room temperature.

(2) 0.2 ml of chloroform (trichloromethylhydrazine) was added, shaked vigorously for 15 seconds, ands allowed to stand for 2-3 minutes at room temperature.

(3) Centrifuged at 12000 g for 15 min at 4° C.

(4) About 500 µl of the supernatant were carefully aspirated into another centrifuge tube (be careful not to extract the protein layer), and 500 µl of isopropanol (special purpose) was added, the mixture was inverted, and allowed to stand for 10 min at room temperature.

(5) Centrifuged at 12000 g for 10 min at 4° C., the supernatant was inverted, and the tip size white substance was seen at the bottom.

(6) 1 ml of 70% ethanol was added to spin wash, and the isopropanol was washed.

(7) After centrifugation at 7500 g at 4° C. for 5 min, the ethanol (try to clean with a pipette tip) was removed and dried for 5-10 minutes; and do not dry it too much or it would be difficult to dissolve, and stored at −70° C.

3. RNA sample quality analysis (NanoDrop1000 spectrophotometer)

The RNA samples were detected with the NanoDrop2000 spectrophotometer. Sample requirements for RNA-seq sequencing were: OD260/OD280≥1.8.

The extracted RNA was subjected to agarose gel electrophoresis. The quality of the RNA sample was detected by using an Agilent 2100 (RNA 6000 Nano kit). The image was observed, photographed and saved on a gel imager. The 28S:18S≥1 and the RIN value ≥7.0 were required.

4. SRNA library construction

The library was constructed by using the Illumina TruSeq Small RNA kit in this experiment. The length of 18-30 nt RNA was recovered from the total RNA and reverse transcribed into single-stranded cDNA by RT-PCR. After amplification of the cDNA, the cDNA product was recovered and a small RNAs library was constructed.

5 Sequencing

The mRNA and miRNA were sequenced by using llumina Hiseq2500/Miseq's second-generation high-throughput sequencing technology. The final data was obtained by processing the data through de-ligating, low-quality, and decontamination processes.

6. Results

Figure 2:
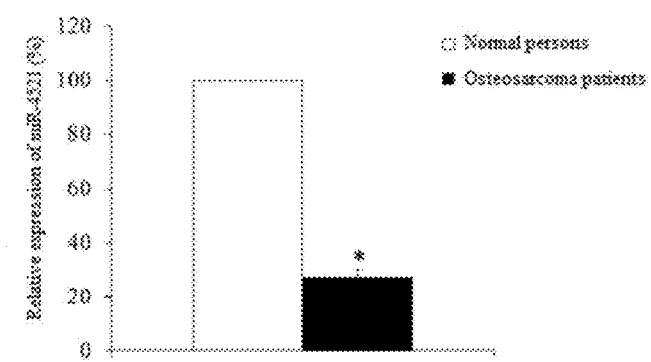
FIG. 2 shows the use of high-throughput sequencing to detect the expression of miR-4521 in the blood of osteosarcoma patients.

After the background of the miRNA raw data was corrected by transcriptome data analysis software, t-test was performed to obtain P value, then Fisher's was used to test and combine P values to screen differentially expressed miRNAs. The p-value <0.01 and the absolute value of $\log_2$ (Fold_change) normalized ≥3 were set as the significance threshold. The results showed that miR-4521, miR-4714-3p, and miR-1292-5p were differentially expressed in normal and osteosarcoma patients. The levels of miR-4714-3p and miR-1292-5p were significantly elevated in the blood of osteosarcoma patients High ($P<0.05$), while miRNA-4521 was significantly down-regulated in the blood of osteosarcoma patients ($P<0.05$). The differential expression of miR-4714-3p was shown in FIG. 1. The results of differential expression of miRNA-4521 were shown in FIG. 2.

Example 2 Qpcr Validation of Differentially Expressed Micrornas 1. miR-4521, miR-4714-3p and miR-1292-5p were selected according to the results of miRNA microarrays for large-scale QPCR validation. According to the sample collection method in Example 1, 50 cases of normal and osteosarcoma samples were collected.

2. The RNA extraction process was the same as in Example 1.

3. Reverse transcription:
1) 10 pg-1 μg total RNA template was mixed with 2 μl 10× buffer, 2 μl dATP (10 mM), 0.5 μl polyA polymerase, 0.5 μl RNase inhibitor and RNase free, the final volume was 20 μl, incubated for 1 h at 37° C.

2) 1 μl of 0.5 μg/μl Oligo(dT) specific RT primer was added to the reaction tube and incubated for 5 min at 70° C.

3) Incubated immediately on ice for at least 2 min to disrupt the secondary structure of RNA and primers.

4) The above 20 μl reaction mixture was mixed with 4 μl 5× buffer, 1 μl dNTP (10 mM), 0.5 μl M-MLV reverse transcriptase, 0.5 μl RNase inhibitor, 10 μl polyA reaction mixture and 4 μl RNA-free RNase free water and incubated at 42° C. for 1 h.

4. QPCR reaction:
1) Primer design
Amplification of miRNA-4521 primers

```
                                       (SEQ ID NO. 4)
Forward primer: GCTAAGGAAGTCCTGTGCTCAG (SEQ ID NO. 5)
Reverse Primer: GTGCAGGGTCCGAGGT
```

Amplification of miR-4714-3p primers

```
                                       (SEQ ID NO. 6)
Forward primer: 5'-CCAACCTAGGTGGTCAGAGTTG-3'
```

Reverse Primer: Universal Reverse Primer (purchased from Beijing Zibo Biotechnology Co., Ltd.)

Amplification of primers for miR-1292-5p

```
                                       (SEQ ID NO. 7)
Forward primer: TGGGAACGGGTTCCGGCAGACGCTG
```

Reverse Primer: Universal Reverse Primer
Amplification of U6 snRNA primers

```
                                       (SEQ ID NO. 8)
Forward primer: CTCGCTTCGGCAGCACA (SEQ ID NO. 9)
Reverse Primer: AACGCTTCACGAATTTGCGT
```

2) A PCR reaction system was prepared according to Table 1 (this system is used to detect miRNA-4521 and miR-4714-3p):

Among them, SYBR Green polymerase chain reaction system was purchased from Invitrogen.

TABLE 1

| PCR reaction system | |
|---|---|
| | Volume |
| SYBR Green Polymerase Chain Reaction System | 12.5 μl |
| Forward primer | 1 μl |
| Reverse primer | 1 μl |
| cDNA template | 2 μl |
| ddH$_2$O | 8.5 μl |
| Total volume | 25 μl |

A PCR reaction system was prepared according to Table 2 (this system is used to detect miR-1292-5p):

TABLE 2

| PCR reaction system | | |
|---|---|---|
| Reaction Components | Concentration | Volume (μl) |
| LightCycler ® 480 SYBR Green I Master | 2× | 5 |

TABLE 2-continued

| PCR reaction system | | |
| --- | --- | --- |
| Reaction Components | Concentration | Volume (μl) |
| Universal primer | 10 μM | 0.2 |
| microRNA-specific primer | 10 μM | 0.2 |
| cDNA | — | 1 |
| Nuclease-free H$_2$O | — | Fill up to 10 μl |

3) PCR reaction conditions:

miR-1292-5p amplification procedure: 95° C. 10 min; 40 cycles (95° C. 10 s, 60° C. 30 s).

The miR-4521 amplification program: 95° C. 10 min, (95° C. 15 s, 60° C. 60 s)×45 cycles.

The miR-4714-3p amplification program: 95° C. 10 min, (95° C. 15 s, 60° C. 55 s)×45 cycles.

SYBR Green was used as a fluorescent marker and PCR reaction was performed on a Light Cycler fluorescence quantitative PCR instrument. Using U6 snRNA as a reference gene, the target band was determined by melting curve analysis and electrophoresis, and relative quantification was performed by the ΔΔCT method.

5. Results

Figure 3:
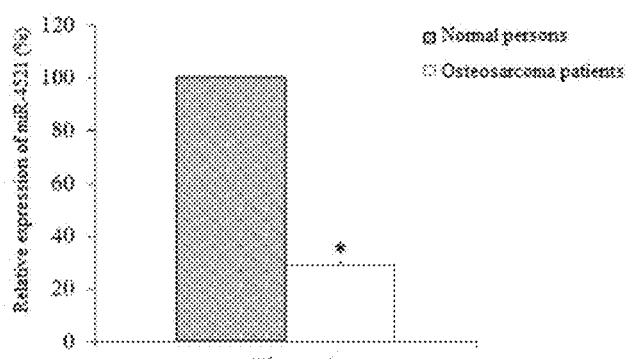
FIG. 3 shows the use of qPCR to detect the expression of miR-4521 in the blood of osteosarcoma patients.
Figure 4:
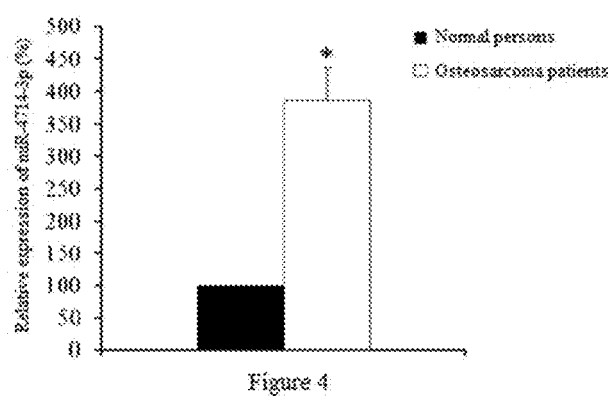
FIG. 4 shows the use of qPCR to detect the expression of miR-4714-3p in the blood of osteosarcoma patients.
Figure 5:
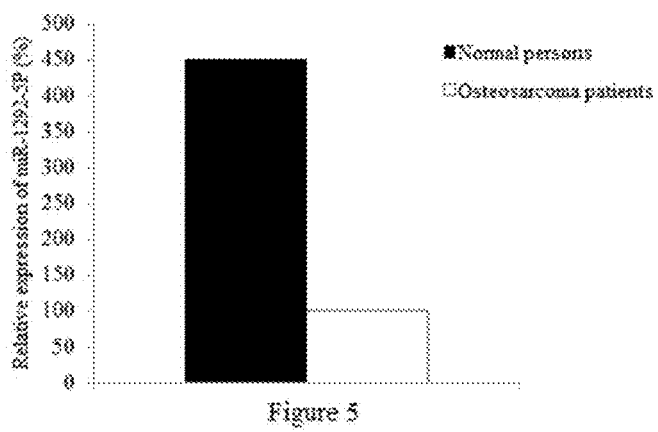
FIG. 5 shows the use of qPCR to detect the expression of miR-1292-5p in the blood of osteosarcoma patients.

Compared with normal human blood, the expression level of miR-4521 in the blood of Osteosarcoma patients was significantly reduced (FIG. 3), while the levels of miR-4714-3p (FIG. 4) and miR-1292-5p (FIG. 5) were significantly elevated (P<0.05).

The above description of the embodiment is only for the purpose of understanding the method of the present invention and its core idea. It should be pointed out that those skilled in the art can make several improvements and modifications to the present invention without departing from the principle of the present invention, and these improvements and modifications will also fall within the protection scope of the present invention.

What is claimed is:

1. A method of treating osteosarcoma comprising:
   a) determining the expression level of miR-4714 in a sample obtained from a subject; and
   b) administering to the subject in need thereof a therapeutically effective amount of a chemotherapeutic agent,
   wherein miR-4714 expression level in the sample above the expression level in a control sample is indicative that the subject has osteosarcoma.

2. The method as claimed in claim 1, wherein the sequence of miR-4714 is shown in SEQ ID NO. 2.

3. The method as claimed in claim 1, wherein the sample comprises blood, urine, cerebrospinal fluid, tissue fluid, sweat, saliva, or tears.

4. The method as claimed in claim 3, wherein the sample is blood.

5. The method as claimed in claim 1, wherein the expression level of miR-4714 is determined by using a chip, or a high-throughput sequencing platform.

* * * * *